United States Patent [19]
Tu et al.

[11] Patent Number: 6,036,689
[45] Date of Patent: Mar. 14, 2000

[54] ABLATION DEVICE FOR TREATING ATHEROSCLEROTIC TISSUES

[76] Inventors: Lily Chen Tu; Hosheng Tu, both of 2151 Palermo, Tustin, Calif. 92782

[21] Appl. No.: 09/159,697

[22] Filed: Sep. 24, 1998

[51] Int. Cl.⁷ .................................................. A61B 17/39
[52] U.S. Cl. ........................... 606/41; 607/122; 607/113; 604/96; 606/194
[58] Field of Search ....................... 604/96–101; 606/191, 606/192, 194, 41, 34; 607/119, 122

[56] References Cited

U.S. PATENT DOCUMENTS

| | | | |
|---|---|---|---|
| 5,456,662 | 10/1995 | Edwards et al. | 604/22 |
| 5,628,313 | 5/1997 | Webster, Jr. | 128/642 |
| 5,722,403 | 3/1998 | McGee et al. | 600/373 |
| 5,782,239 | 7/1998 | Webster, Jr. | 600/374 |
| 5,885,278 | 3/1999 | Fleischman | 606/41 |
| 5,891,135 | 4/1999 | Jackson et al. | 606/41 |
| 5,904,680 | 5/1999 | Kordis et al. | 606/41 |
| 5,925,038 | 2/1999 | Panescu et al. | 606/41 |

OTHER PUBLICATIONS

Gabriel Spera "The Next Wave in Minimally Invasive Surgery" MD & DI pp. 36–44 Aug. 1998.

*Primary Examiner*—Linda C. M. Dvorak
*Assistant Examiner*—David M. Ruddy

[57] ABSTRACT

An ablation device for treating atherosclerotic tissues of a patient, the ablation device comprising a catheter shaft and an inner catheter, the inner catheter having a deployable electrode means, wherein the deployable electrode means comprises a plurality of preshaped expandable metallic basket members at the distal end of the inner catheter adapted to contact the atherosclerotic tissues and to apply RF current to the tissues for therapeutic purposes. Alternately, a plurality of expandable metallic basket members are wrapped onto and around a balloon of an ablation device system.

12 Claims, 7 Drawing Sheets

ABLATION DEVICE FOR TREATING ATHEROSCLEROTIC TISSUES

The present invention generally relates to improved medical device and methods for treating tissues, and more particularly, to such an ablation device and methods for treating atherosclerotic tissues in a patient by delivering therapeutic RF energy through an expandable basket structure having means for providing a plurality of continuous linear electrodes to the specific lesion sites.

BACKGROUND OF THE INVENTION

An artery is one of the tube-shaped blood vessels that carry blood away from a heart to the body's tissues and organs. An artery is made up of an outer fibrous layer, a smooth muscle layer, a connecting tissue layer, and the inner lining cells. If arterial walls become hardened due to the accumulation of fatty substances, then blood flow can be diminished. Hardening of the arteries, or loss of vessel elasticity, is termed arteriosclerosis while fatty deposit build-up is termed atherosclerosis. Atherosclerosis and its complications are a major cause of death in the United States. Heart and brain diseases are often the direct result of this accumulation of fatty substances that impair the arteries' ability to nourish vital body organs.

Balloon angioplasty is a nonsurgical method of clearing coronary and other arteries, blocked by atherosclerotic plaque, fibrous and fatty deposits on the walls of arteries. A catheter with a balloon-like tip is threaded up from the arm or groin through the artery until it reaches the blocked area. The balloon is then inflated, flattening the plaque and increasing the diameter of the blood vessel opening. The arterial passage is thus widened. As a result of enlarging the hardened plaque, cracks may unfortunately occur within the plaque to expose the underlying fresh tissue or denuded cells to the blood stream.

There are limitations, however, to this technique's application, depending on the extent of the disease, the blood flow through the artery, and the part of the anatomy and the particular vessels involved. Plaque build-up and/or severe re-stenosis recurrence within 6 months is up to 30–40 percent of those treated. Balloon angioplasty can only be characterized as a moderate-success procedure. Recently, a newer technique of inserting a metallic stenting element is used to permanently maintain the walls of the vessel treated at its extended opening state. Vascular stents are tiny mesh tubes made of stainless steel or other metals and are used by heart surgeons to prop open the weak inner walls of diseased arteries. They are often used in conjunction with balloon angioplasty to prevent restenosis after the clogged arteries are treated. Stenting technique reduces the probability of restenosis; however, the success rate is still sub-optimal. The underlying fresh tissue or damaged cells still pose as a precursor for vessel reclosures or restenosis, regardless of stenting or not.

When a clogged artery is widened, the plaque is broken up and the underlying collagen or damaged endothelium is exposed to the blood flow. Collagen has a prothrombotic property, which is a part of the body healing process. Unless the collagen or the damaged endothelium is passivated or modulated, the chance for blood vessel clotting as well as restenosis still exists. Moderate heat is known to tighten and shrink the collagen tissue as illustrated in U.S. Pat. No. 5,456,662 and U.S. Pat. No. 5,546,954. It is also clinically verified that thermal energy is capable of denaturing the tissue and modulating the collagenous molecules in such a way that treated tissue becomes more resilient ("The Next Wave in Minimally Invasive Surgery" MD&DI pp. 36–44, August 1998). Therefore, it becomes imperative to post-treat vessels walls after the walls are treated with angioplasty and/or stenting procedures.

One method of reducing the size of cellular tissues in situ has been used in the treatment of many diseases, or as an adjunct to surgical removal procedures. This method applies appropriate heat to the tissues, and causes them to shrink and tighten. It can be performed on a minimal invasive fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissue contact site to obtain the desired temperature for treating a tissue.

To effect the optimal ablation, it requires selection of the most appropriate device-to-tissue contact site as well as the most effective contact surface area. Several recent patents disclose a catheter in a basket structure having means for providing a plurality of discrete and isolated point electrodes. The patents include U.S. Pat. No. 4,699,147 to Chilson et al., No. 5,156,151 to Imran, No. 5,255,679 to Imran, No. 5,345,936 to Pomeranz et al., No. 5,411,025 to Webster, Jr., No. 5,628,313 to Webster, Jr., No. 5,636,634 to Kordis et al., and No. 5,672,153 to Lax et al. However, all of the above-identified patents comprise a non-conductive spacing between any two electrodes. A major drawback of those patents is obvious because of its limited electrode contact surface to the tissues for delivering heat therapy.

A plurality of temporary metallic members, such as the long continuous electrodes on a basket-type catheter probe, is useful for delivering the RF thermal energy to the denuded collagen or damaged endothelium to shrink and tighten the target tissue after an angioplasty procedure. Therefore, there is a need for an improved medical device having the capability to effectively contact the inner walls of a tubular vessel using the radiofrequency energy to treat an enlarged artery or other tissues, such as esophagus, larynx, uterus, urethra and the like.

SUMMARY OF THE INVENTION

In general, it is an object of the present invention to provide a method and an improved medical ablation device for generating heat, to treat the atherosclerotic vascular vessels, or other tissues/organs, such as intestine, colon, uterus, urethra tube, and the like. It is another object of the present invention to provide a method and a device for monitoring the temperature of the ablated tissue, and to control the temperature by utilizing a temperature control mechanism and/or algorithm. The location of the temperature sensor means is preferably at close proximity of the electrode means of the ablation device. It is still another object of this invention to provide a method and an device for treating atherosclerotic tissues, vascular walls, or tubular cellular tissues by applying RF current to the metallic members of a basket-type catheter probe system having a plurality of metallic electrodes and subsequently to the underlying tissues.

Briefly, heat is generated by supplying a suitable energy source to a device, which is comprised of an electrode means, in contact with the body tissues. "An electrode means" is defined in this invention as a basket-type catheter probe having a plurality of basket members, wherein each basket member is a linear continuous metallic electrode. Each basket member may be in a mesh form, a coil form, a curved wire form, or other appropriate form, used to contact the tissues or enlarged vessels. A suitable energy source may consist of radiofrequency energy, microwave energy, ultrasonic energy, alternating current energy, or laser energy. The energy can be applied to the metallic basket member and subsequently to the atherosclerotic vascular walls or cellular tissues through the electrode means. A DIP (dispersive indifferent pad) type pad or electrode that contacts the patient, is connected to the Indifferent Electrode Connector on the RF generator. Therefore, the RF current delivery becomes effective when a close circuit from a RF generator through a patient and returning to the RF generator is formed. When using an alternating current outlet, the generator should be grounded to avoid electrical interference. Heat is controlled by the power of the RF current delivered and by the delivery duration. The standard RF current generator means and its applications through the electrode means, to a patient are well known for those who are skilled in the art.

In an optional embodiment, means for generating vibration at the distal section comprises a motor mounted in the cavity of the handle, which has a rotatable motor shaft, an elongated connecting shaft having a first end, to which the distal end portion of the catheter probe is connected, and a second end connected to the handle, a weight eccentrically mounted on the motor shaft with respect to the motor shaft axis, so as to rotate eccentrically, so that when the motor shaft rotates, the distal end portion of the device vibrates.

In one embodiment, the device comprises a deployable electrode means. In a preferred embodiment, the electrode means is a basket-type plurality of basket members wrapped onto and around a balloon of a catheter system. The resilience and semi-compressibility of the basket members become the property of the electrode means to ultimately deploy to its full extent by the balloon. It is also to apply appropriate pressure to ensure intimate tissue contact when applying RF therapy. The deployed basket members of the electrode means are to intimately contact the tissues behind each basket member. The electrode means is connected to an external RF generating means through an electrical conductor. In an alternate embodiment, the basket members of the electrode means may be preshaped and extends to its maximum distance radially to contact the tissues when deployed. The deployment of the expandable basket members of the catheter probe can be accomplished either by the preshaped metallic members or by the pushing force from an inflated balloon.

The method and medical device of the present invention has several significant advantages over other known systems or techniques to treat the atherosclerotic tissues after the tissue is enlarged. In particular, the device system comprising a deployable electrode means having a basket-type catheter probe with a plurality of linear continuous metallic electrodes and using RF energy as a heat source in this invention results in a more efficient therapeutic effect, which is highly desirable in its intended application.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 5, what is shown is an embodiment of the ablation device system, comprising applying radiofrequency energy therapy to treat the atherosclerotic vascular vessels, or other tubular cellular tissues of a patient through a basket-type preshaped expandable metallic basket members or through the expansion force from an inflatable balloon on the expandable metallic basket members.

Figure 1:
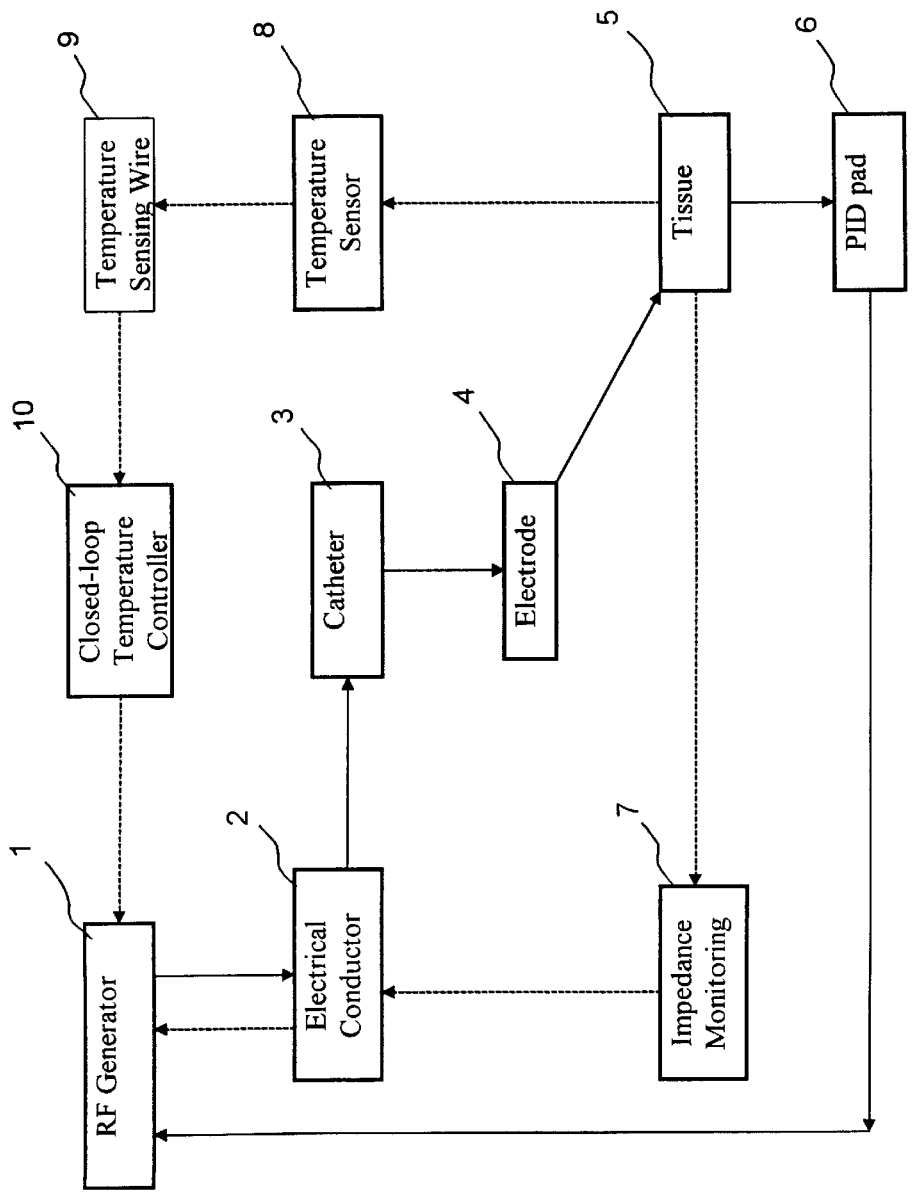
FIG. 1 is a schematic diagram of a RF treatment method in relation to the tissue or atherosclerotic tissue through an electrode means of a catheter in a patient.

FIG. 1 shows a schematic diagram of a RF treatment method in relation to the tissues or atherosclerotic tissues through an electrode means of a catheter in a patient. A RF generator 1 is connected to a catheter or an ablation device 3 through an electrical conductor 2. An electrode means 4 of the catheter 3 is to contact the tissue 5 of a patient when the device is deployed. The electrode is in close contact with the underlying tissue 5. A DIP (dispersive indifferent pad) type pad 6 that contacts a patient is connected to the Indifferent Electrode Connector on the RF generator 1. Therefore, the RF current delivery becomes effective when a close circuit from a RF generator through a patient and returning to the RF generator is formed. Impedance 7 measured from the tissue contact is to ensure good tissue contact for ablation, otherwise the RF current is cutoff when the impedance is unreasonably high. A temperature sensor 8 is used to measure the tissue temperature and is relayed through a temperature sensing wire 9 and a closed-loop temperature controller 10 for controlling the ablative energy delivered. Heat is controlled by the power of the RF current delivered and by the delivery duration.

Figure 2:
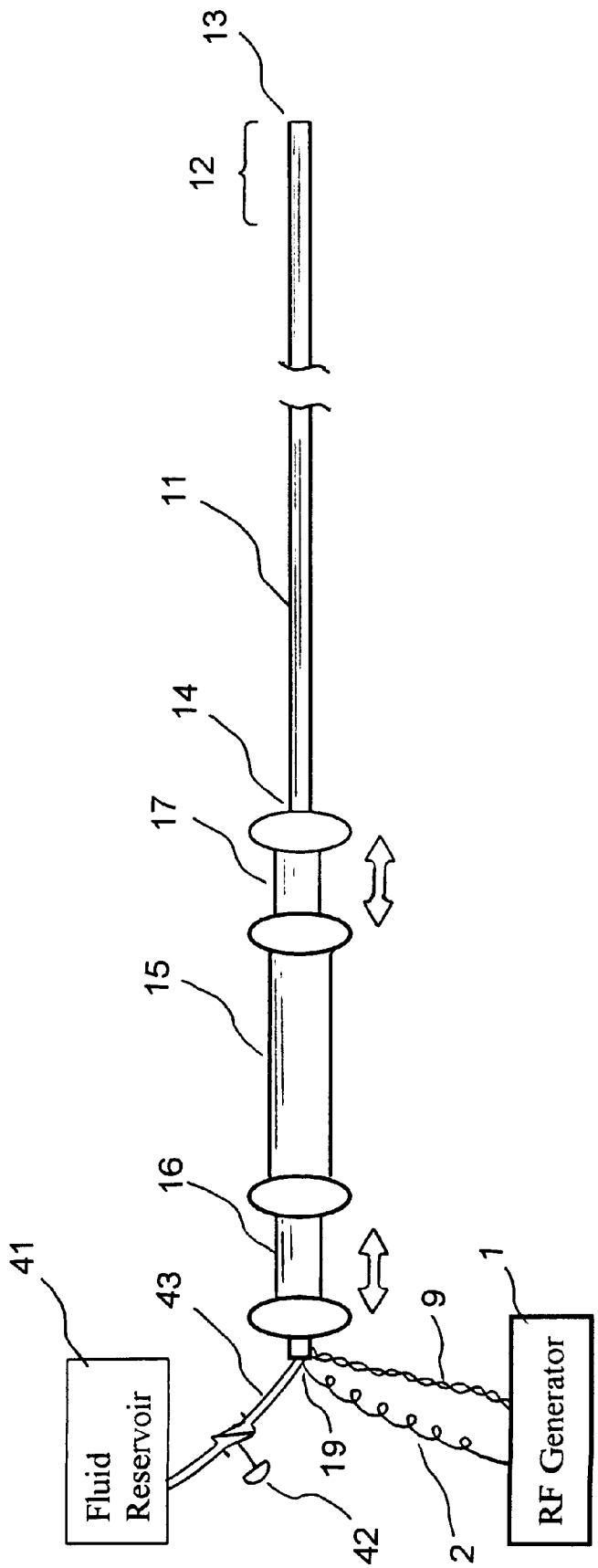
FIG. 2 is an overall view of the ablation device system having a deployable electrode means and a RF generator, constructed in accordance to the principles of the present invention.

As shown in FIG. 2, the ablation device system comprises a catheter shaft 11, the catheter shaft having a distal section 12, a shaft distal end 13, a shaft proximal end 14, and at least one lumen 18 extending between the shaft proximal end 14 and the shaft distal end 13, wherein the at least one lumen IS has at least one opening 61 at the shaft distal end 13 of the catheter shaft 11. A handle 15 is attached to the shaft proximal end 14 of the catheter shaft 11, wherein the handle 15 has a cavity.

An inner catheter 21 is located inside the at least one lumen 18 of the catheter shaft 11, wherein the inner catheter 21 comprises a distal end 25 and a proximal end. An electrode means 4 is mounted at the distal end 25 of the inner catheter 21, wherein the electrode means 4 comprises a plurality of non-preshaped expandable metallic basket members 4A–4H or preshaped expandable metallic basket members 4I–4L, each metallic basket member having a basket distal end, a basket proximal end, wherein the basket proximal ends of the expandable metallic basket members are joined at the distal end 25 of the inner catheter 21 and wherein the basket distal ends of the expandable metallic basket members are joined at a distal joint 22.

An electrode deployment mechanism 17 is mounted on the handle 15, wherein the electrode deployment mechanism 17 is attached to the proximal end of the inner catheter 21, wherein the plurality of preshaped expandable metallic basket members is expanded at a deployed state, and wherein the plurality of preshaped expandable metallic basket members is retracted at a non-deployed state. The ablation catheter system comprises a RF current generating means 1, wherein the RF current is supplied to the electrode means 4 for therapeutic purposes. In an additional embodiment, a fluid reservoir 41 is provided for delivering pressurized working fluid through a control valve 42 and a conveying duct 43 to the inflatable balloon 53.

Figure 3:
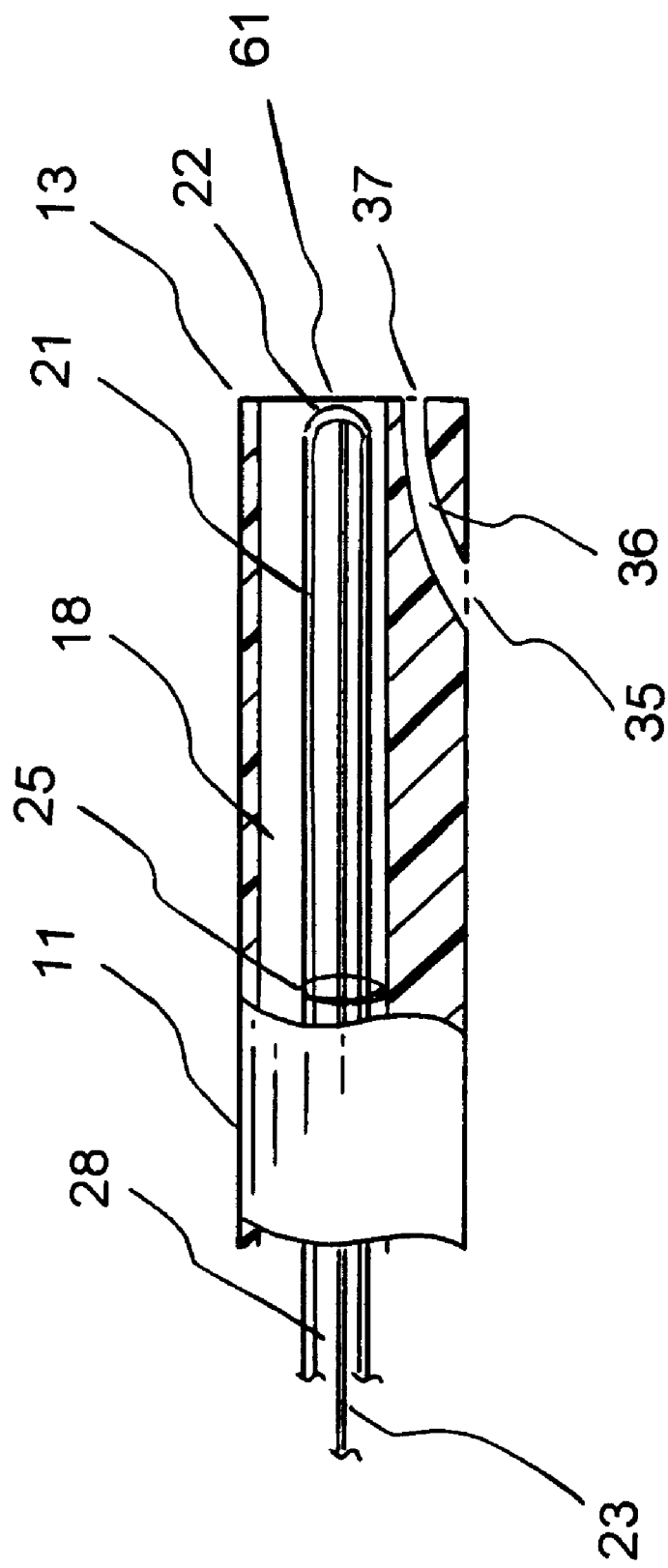
FIG. 3 is a cross-sectional view of the distal end portion of the device, the device having a deployable electrode means positioned within the lumen of an inner catheter at a non-deployed state.

FIG. 3 shows a cross-sectional view of the distal end portion 12 of the device, wherein the device has a deployable electrode means 4 positioned within the lumen 18 of the inner catheter 21 at a non-deployed state. In one embodiment, the shaft distal end 13 has two lumens 18 and 36. One lumen 18 is used by the deployable inner catheter 21. The other lumen 36, a wire guide lumen is used to tract a previously inserted guidewire to the lesion site. In an alternate embodiment, the ablation device of the present invention rides on an existing guidewire to the target site 5 for ablation operation.

The ablation device system further comprises a lumen 28 between the proximal end and the distal end 25 of the inner catheter 21, and further comprises a connecting shaft 23 inside said lumen 28 of the inner catheter 21. The connecting shaft 23 has a distal end and a proximal end, wherein the distal end of the connecting shaft 23 is joined to the distal joint 22 of the metallic basket members, and wherein the proximal end of the connecting shaft is secured to the electrode deployment mechanism 17. A special push-pull controller 16 on the handle adapted for the push-pull operation of the connecting shaft 23 is part of the electrode deployment mechanism 17.

An insulated electrical conductor 2 or the inner catheter itself as a conducting means passes through the lumen 18 of the catheter shaft 11 and is connected to the electrode means 4. The other end of the electrical conductor means is connected to an external RF generator 1.

Figure 4:
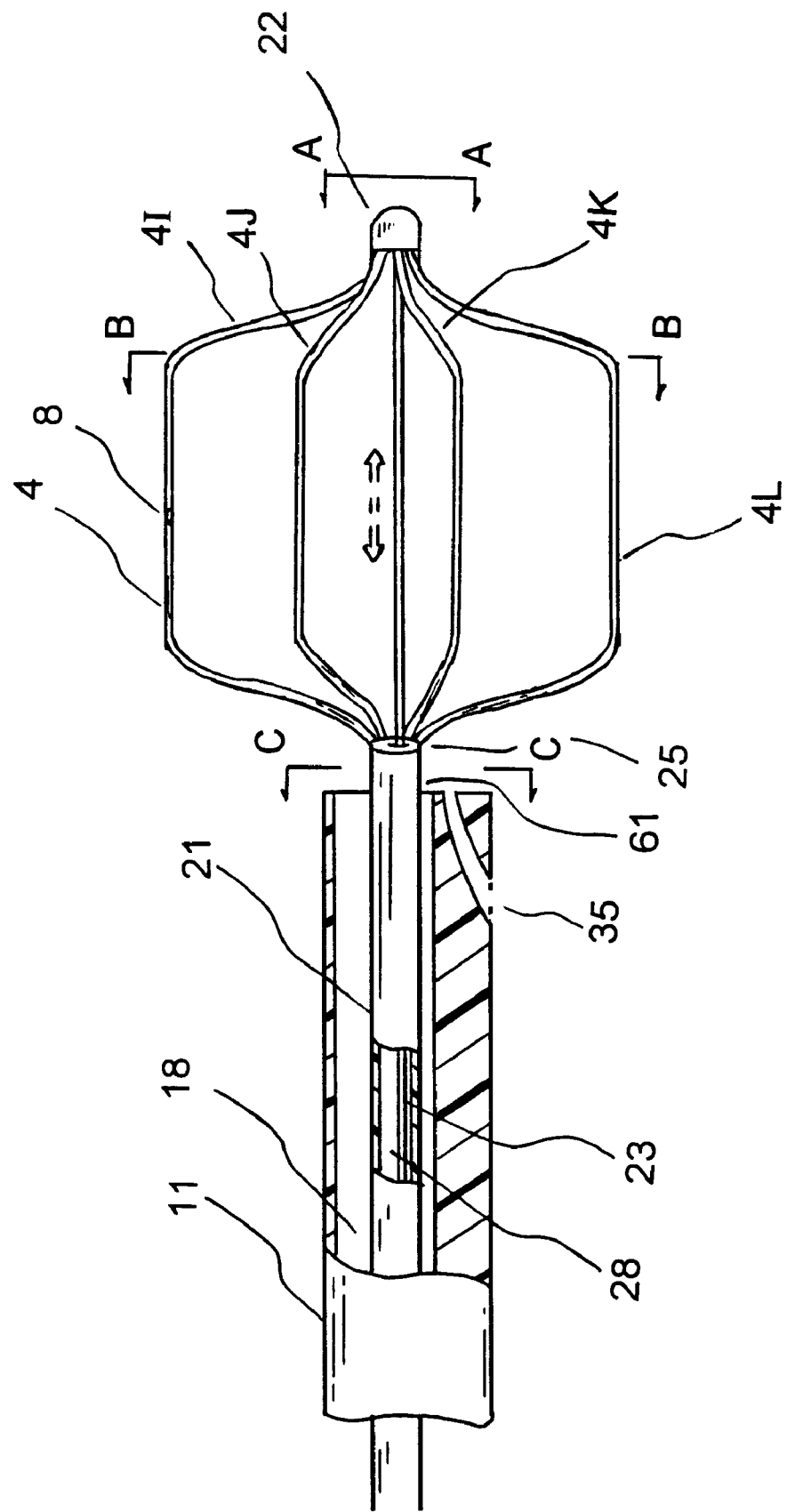
FIG. 4 is a cross-sectional view of the distal end portion of the device, the device having a deployable electrode means comprising a plurality of preshaped expandable metallic basket members at a deployed state.

FIG. 4 shows a cross-sectional view of the distal end portion of the device, wherein the device has a deployable electrode means 4 comprising a plurality of preshaped expandable metallic basket members at a deployed state. The deployment operation is initiated at the electrode deployment mechanism 17 at the handle 15. The deployed plurality of metallic basket members 4I–4L are fully extended radially to contact an inside surface of the vascular wall, as a result of its preshaped memory. This portion of the deployed metallic basket members is made of conductive material, which is connected to the RF current through an insulated electrical conductor. Other portion of the catheter shaft and the surface of the inner catheter are not conductive.

In one embodiment, at least one temperature sensing means 8 is disposed at close proximity of the electrode means 4. Insulated temperature sensor wire means 9 passes from the temperature sensing means 8, to an external temperature control mechanism 10 through an outlet connector 19. The RF current delivery is controlled by using the measured temperature from the temperature sensing means 8, through a closed-loop temperature control mechanism 10 and/or algorithm. When the measured temperature rises to a preset high-limit point, the temperature control mechanism sends out a signal to cut off the RF current supply. In a similar manner, when the measured temperature drops to a preset low-limit point, the temperature control mechanism sends out a signal to activate the RF current supply.

Figure 4A:
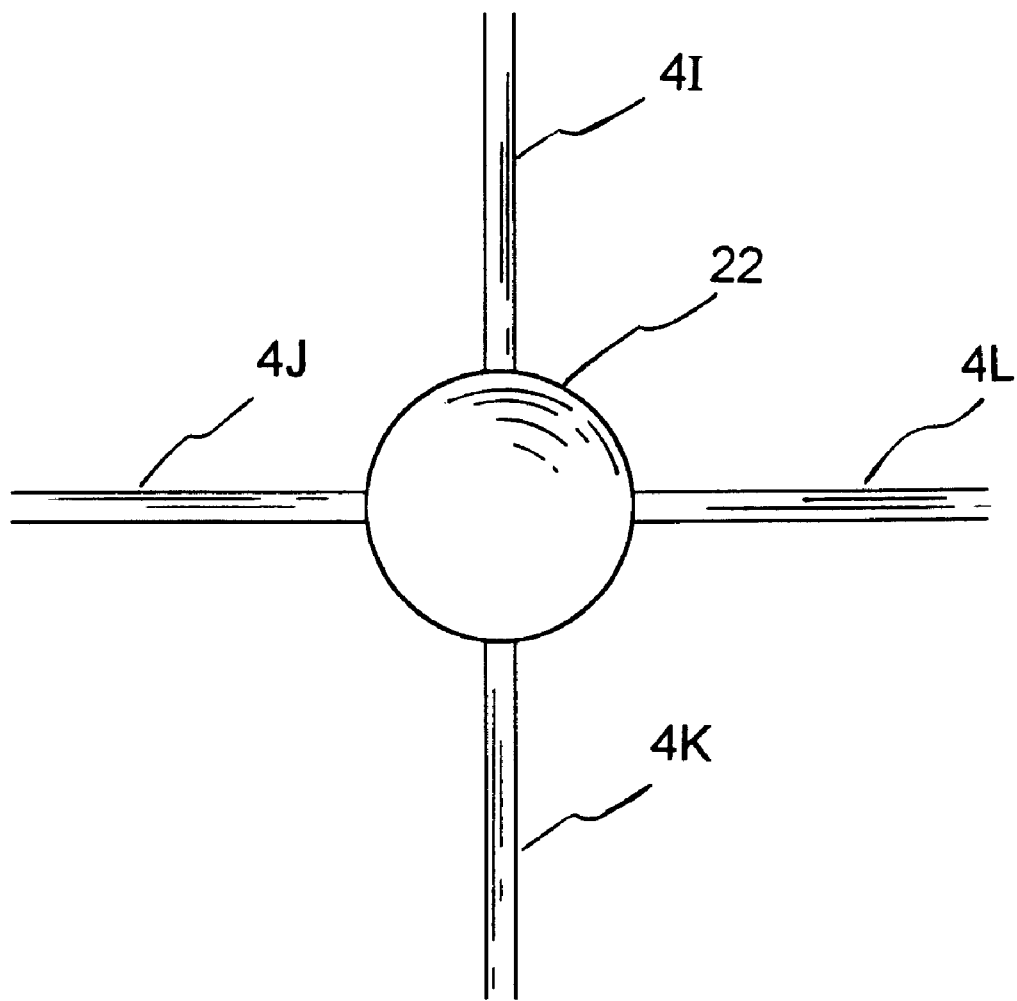
FIG. 4A is a transverse view, section A—A of FIG. 4.
Figure 4B:
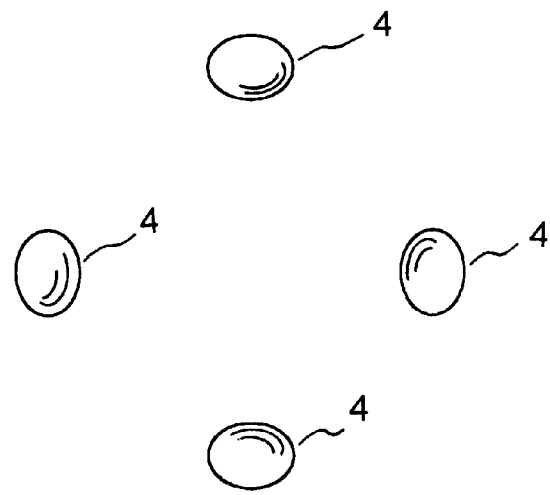
FIG. 4B is a transverse view, section B—B of FIG. 4.
Figure 4C:
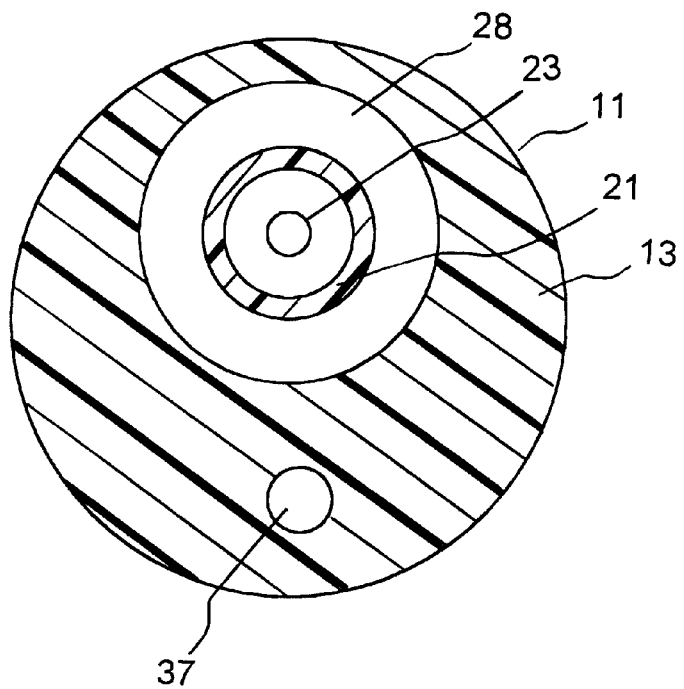
FIG. 4C is a transverse view, section C—C of FIG. 4.

FIG. 4A shows a transverse view, section A—A of FIG. 4. The distal ends of all metallic basket members 4I, 4J, 4K, and 4L are secured to a distal joint 22. FIG. 4B shows a transverse view, section B—B of FIG. 4. In one optional embodiment, the cross-section of the metallic basket members is an oval shape or flat shape. FIG. 4C shows a transverse view, section C—C of FIG. 4. In a preferred embodiment, a portion of the preshaped expandable metallic basket members is essentially straight at a deployed state.

Figure 5:
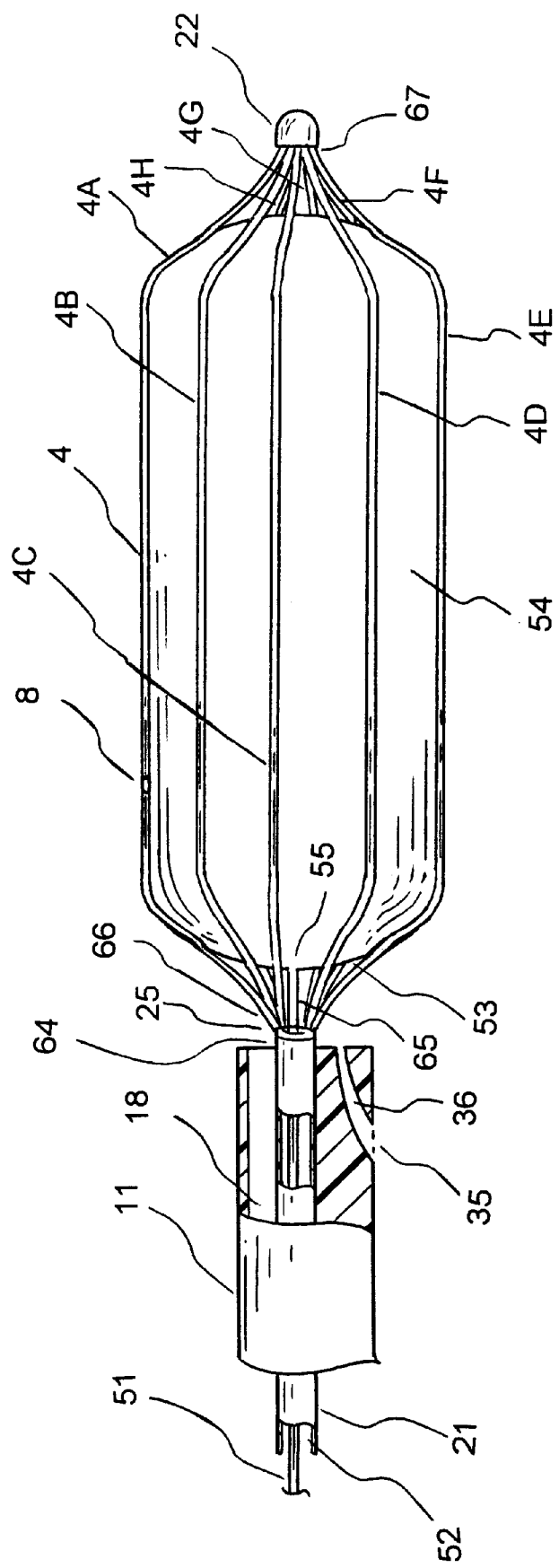
FIG. 5 is a cross-sectional view of the distal end portion of an alternate device, the device having a deployable electrode means comprising a plurality of expandable metallic basket members wrapped onto and around an inflatable balloon at a deployed state.

FIG. 5 shows a cross-sectional view of the distal end portion of an alternate device, wherein the device has a deployable electrode means comprising a plurality of expandable metallic basket members wrapped onto and around an inflatable balloon at a deployed state. An alternate ablation device system comprises a catheter shaft 11 having a distal section 12, a shaft distal end 13, a shaft proximal end 14, and at least one lumen 18 extending between the shaft proximal end 14 and the shaft distal end 13, wherein the at least one lumen 18 has at least one opening 64 at the shaft distal end 13 of the catheter shaft 11.

A handle 15 is attached to the shaft proximal end 14 of the catheter shaft 11, wherein the handle has a cavity. An inner catheter 21 is located inside the at least one lumen 18 of the catheter shaft 11, wherein the inner catheter 21 comprises a distal end 25, a proximal end, and at least one lumen 52 extending between the distal end and the proximal end. An inflation tubing 65 is an extension of an inflation lumen 51, wherein the inflation lumen 51 is located within the inner catheter 21 and is communicated to the external fluid reservoir 41 through the fluid conveying duct 43. The inflation tubing 65 extends distally to the distal end 25 of the inner catheter 21, the inflation tubing 65 having a proximal end and a distal end 55.

The alternate ablation device further comprises an inflatable balloon 53 having a proximal end and a distal end, wherein the distal end 55 of the inflation tubing 65 opens into and is in communication with an interior of the inflatable balloon 53, the distal end of the inflatable balloon 53 is sealed;

In the alternate ablation device system, an electrode means 4 is mounted at the distal end 25 of the inner catheter 21, wherein the electrode means comprises a plurality of expandable metallic basket members 4A–4H wrapped onto and around the inflatable balloon 53, each expandable metallic basket member having a basket distal end 67 and a basket proximal end 66, wherein the basket proximal ends of the expandable metallic basket members are joined at the distal end 25 of the inner catheter 21 and wherein the basket distal ends of the expandable metallic basket members are joined at a distal joint 22. An electrode deployment mechanism 17 is mounted on the handle 15, wherein the electrode deployment mechanism 17 is attached to the proximal end of the inner catheter 21, wherein the plurality of expandable metallic basket members is expanded at a deployed state, and wherein the plurality of expandable metallic basket members is retracted at a non-deployed state.

The ablation system also comprises a RF current generating means 1, wherein the RF current is supplied to the electrode means 4 for therapeutic purposes.

The ablation device system further comprises a wire guide shaft at the distal section 12 of the catheter shaft 11, the wire guide shaft defining a wire guide lumen 36, the wire guide shaft having a proximal end 35 and a distal end 37, wherein the distal end 37 of the wire guide shaft is proximal to the proximal end of the inflatable balloon 53, and the wire guide shaft is coupled only to the tip section 12 of the catheter shaft 11 completely proximally of the proximal end of the inflatable balloon 53.

A method for treating atherosclerotic tissues of a patient using an ablation device system is illustrated. The ablation device system comprises a catheter shaft 11 and an inner catheter 21, the inner catheter having a proximal end, a distal end and a deployable electrode means 4 mounted at the distal end of the inner catheter, wherein the electrode means comprises a plurality of preshaped expandable metallic basket members, each metallic basket member having a basket distal end, a basket proximal end, wherein the basket proximal ends of the metallic basket members are joined at the distal end of the inner catheter and wherein the basket distal ends of the metallic basket members are joined at a distal joint. The device system further comprises a RF current generating means, wherein the RF current is supplied to the electrode means. The method comprises the steps of: (a) inserting the ablation device through an artery or a vein to the location of the atherosclerotic tissues; (b) deploying the electrode means to expand the preshaped expandable metallic basket members adapted to contact the atherosclerotic tissues; and (c) applying RF current to the electrode means to effect treatment of the atherosclerotic tissues.

As an alternative illustration, a method for treating atherosclerotic tissues of a patient using an ablation device system is illustrated. The method comprises the steps of: (a) inserting the ablation device through an artery or a vein to the location of the atherosclerotic tissues; (b) deploying the electrode means to expand the expandable metallic basket members adapted to contact the atherosclerotic tissues; and (c) applying RF current to the electrode means to effect treatment of the atherosclerotic tissues. The alternate ablation device system comprises: a catheter shaft having a distal section, a shaft distal end, a shaft proximal end, and at least one lumen extending between the shaft proximal end and the shaft distal end, wherein the at least one lumen has at least one opening at the shaft distal end of the catheter shaft; a handle attached to the shaft proximal end of the catheter shaft, wherein the handle has a cavity; an inner catheter located inside the at least one lumen of the catheter shaft, wherein the inner catheter comprises a distal end, a proximal end, and at least one lumen extending between the distal end and the proximal end; an inflation tubing extending distally to the distal end of the inner catheter, the inflation tubing having a proximal end and a distal end; an inflatable balloon having a proximal end and a distal end, wherein the distal end of the inflation tubing opens into and is in communication with an interior of the inflatable balloon, the distal end of the inflatable balloon is sealed; an electrode means mounted at the distal end of the inner catheter, wherein the electrode means comprises a plurality of expandable metallic basket members wrapped onto and around the inflatable balloon, each expandable metallic basket member having a basket distal end and a basket proximal end, wherein the basket proximal ends of the expandable metallic basket members are joined at the distal end of the inner catheter and wherein the basket distal ends of the expandable metallic basket members are joined at a distal joint; an electrode deployment mechanism mounted on the handle, wherein the electrode deployment mechanism is attached to the proximal end of the inner catheter, wherein the plurality of expandable metallic basket members is expanded at a deployed state, and wherein the plurality of expandable metallic basket members is retracted at a non-deployed state; and a RF current generating means, wherein the RF current is supplied to the electrode means.

The external RF current generator means has the capability to supply RF current by controlling the time, power, and temperature through an optional separate closed-loop temperature control means. The patient is connected to the RF generator means through a DIP electrode to form a closed-loop current system Therefore, RF current is supplied and delivered to the targeted atherosclerosis region, through the electrode means of this invention. The radiofrequency energy current in this invention is preferably within the range of 50 to 2,000 kHz. The frequency of the vibration of the medical device in this invention is preferably within the range of 60 to 1000 cycles per minute. By simultaneously applying RF energy to the electrode and by applying the vibrational pressure therapy, the atherosclerotic tissues can be treated.

In a particular embodiment, the material for the electrode means of this invention consists of conductive metals such as platinum, iridium, gold, silver, stainless steel, Nitinol, or an alloy of these metals.

From the foregoing description, it should now be appreciated that an ablation device system for the tubular organs, atherosclerotic tissues, and the treatment of vascular tissues, comprising a suitable energy source and a pressure therapy has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An ablation device system comprising:
   A catheter shaft having a distal section, a shaft distal end, a shaft proximal end, and at least one lumen extending between the shaft proximal end and the shaft distal end, wherein the at least one lumen has at least one opening at the shaft distal end of the catheter shaft;
   a handle attached to the shaft proximal end of the catheter shaft, wherein the handle has a cavity;
   an inner catheter located inside the at least one lumen of the catheter shaft, wherein the inner catheter comprises a distal end, a proximal end, and at least one lumen extending between the distal end and the proximal end;
   an inflation tubing extending distally to the distal end of the inner catheter, the inflation tubing having a proximal end and a distal end;

an inflatable balloon having a proximal end and a distal end, wherein the distal end of the inflation tubing opens into and is in communication with an interior of the inflatable balloon, wherein the distal end of the inflatable balloon is sealed;

an electrode arrangement mounted at the distal end of the inner catheter, wherein the electrode arrangement comprises a plurality of expandable metallic basket members wrapped onto and around the inflatable balloon, each expandable metallic basket member having a basket distal end and a basket proximal end, wherein the basket proximal ends of the expandable metallic basket members are joined at the distal end of the inner catheter and wherein the basket distal ends of the expandable metallic basket members are joined at a distal joint;

an electrode deployment mechanism mounted on the handle, wherein the electrode deployment mechanism is attached to the proximal end of the inner catheter, wherein the plurality of expandable metallic basket members are expanded at a deployed state, and wherein the plurality of expandable metallic basket members are retracted at a non-deployed state;

a RF current generating means, wherein the RF current is supplied to the electrode arrangement for therapeutic purposes; and a wire guide shaft at the distal section of the catheter shaft, the wire guide shaft defining a wire guide lumen, the wire guide shaft having a proximal end and a distal end, wherein the distal end of the wire guide shaft is proximal to the proximal end of the inflatable balloon, and the wire guide shaft is coupled only to the tip section of the catheter shaft completely proximally of the proximal end of the inflatable balloon.

2. The ablation device system as in claim 1 further comprising at least one temperature sensor, wherein the temperature sensor is disposed at close proximity of the electrode arrangement of the inner catheter.

3. The ablation device system as in claim 2 further comprising a temperature control means, wherein a temperature measured from the temperature sensor is relayed to the temperature control means and is adapted to effect the RF current supply to the ablation device system.

4. The ablation device system of claim 1, wherein the RF current is within the range of 50 to 2,000 kHz.

5. The ablation device system of claim 1, wherein a material for the expandable metallic basket members of the electrode arrangement is selected from the group consisting of platinum, iridium, gold, silver, stainless steel, Nitinol, and an alloy of their mixtures.

6. The ablation device system of claim 1, wherein a portion of the expandable metallic basket members is essentially straight.

7. A method for treating atherosclerotic tissues of a patient using an ablation device system, the ablation device system comprising A catheter shaft having a distal section, a shaft distal end, a shaft proximal end, and at least one lumen extending between the shaft proximal end and the shaft distal end, wherein the at least one lumen has at least one opening at the shaft distal end of the catheter shaft;

a handle attached to the shaft proximal end of the catheter shaft, wherein the handle has a cavity;

an inner catheter located inside the at least one lumen of the catheter shaft, wherein the inner catheter comprises a distal end, a proximal end, and at least one lumen extending between the distal end and the proximal end;

an inflation tubing extending distally to the distal end of the inner catheter, the inflation tubing having a proximal end and a distal end;

an inflatable balloon having a proximal end and a distal end, wherein the distal end of the inflation tubing opens into and is in communication with an interior of the inflatable balloon, wherein the distal end of the inflatable balloon is sealed;

an electrode arrangement mounted at the distal end of the inner catheter, wherein the electrode arrangement comprises a plurality of preshaped expandable metallic basket members wrapped onto and around the inflatable balloon, each expandable metallic basket member having a basket distal end and a basket proximal end, wherein the basket proximal ends of the expandable metallic basket members are joined at the distal end of the inner catheter and wherein the basket distal ends of the expandable metallic basket members are joined at a distal joint;

an electrode deployment mechanism mounted on the handle, wherein the electrode deployment mechanism is attached to the proximal end of the inner catheter, wherein the plurality of preshaped expandable metallic basket members are expanded at a deployed state, and wherein the plurality of expandable metallic basket members are retracted at a non-deployed state;

a RF current generating means, wherein the RF current is supplied to the electrode arrangement for therapeutic purposes; and a wire guide shaft at the distal section of the catheter shaft, the wire guide shaft defining a wire guide lumen, the wire guide shaft having a proximal end and a distal end, wherein the distal end of the wire guide shaft is proximal to the proximal end of the inflatable balloon, and the wire guide shaft is coupled only to the tip section of the catheter shaft completely proximally of the proximal end of the inflatable balloon;

The method comprising the steps of:

(a) inserting the ablation device through an artery or a vein to the location of the atherosclerotic tissues;

(b) deploying the electrode arrangement to expand the preshaped expandable metallic basket members adapted to contact the atherosclerotic tissues; and (c) applying RF current to the electrode arrangement to effect treatment of the atherosclerotic tissues.

8. The method for treating atherosclerotic tissues of a patient using an ablation device system as in claim 7, the method further comprising the ablation device system comprising at least one temperature sensor, wherein the temperature sensor is disposed at close proximity of the electrode arrangement of the inner catheter.

9. The method for treating atherosclerotic tissues of a patient using an ablation device system as in claim 7, the method further comprising the ablation device system comprising a temperature control means, wherein a temperature measured from the temperature sensor is relayed to the temperature control means and adapted to effect the RF energy supply to the electrode means.

10. The method for treating atherosclerotic tissues of a patient using an ablation device system as in claim 7, the method further comprising the ablation device system having a RF current delivery within the range of 50 to 2,000 kHz.

11. The method for treating atherosclerotic tissues of a patient using an ablation device system as in claim 7, wherein a material for the electrode arrangement is selected from the group consisting of platinum, iridium, gold, silver, stainless steel, Nitinol, and an alloy of their mixtures.

12. The method for treating atherosclerotic tissues of a patient using an ablation device system as in claim 7, wherein a portion of the preshaped expandable metallic basket members is essentially straight.

* * * * *